US008084494B2

(12) United States Patent
De Kock et al.

(10) Patent No.: US 8,084,494 B2
(45) Date of Patent: Dec. 27, 2011

(54) SUBSTITUTED AMINOPHENYLSULFONAMIDE COMPOUNDS AS HIV PROTEASE INHIBITOR

(75) Inventors: Herman Augustinus De Kock, Arendonk (BE); Tim Hugo Maria Jonckers, Edegem (BE); Stefaan Julien Last, Lint (BE); Paul Jozef Gabriel Maria Boonants, Mechelen (BE); Dominique Louis Nestor Ghislain Surleraux, Braine-le-château (BE); Piet Tom Bert Paul Wigerinck, Terhagen (BE)

(73) Assignee: Tibotec Pharmaceuticals Ltd., Little Island (IE)

( * ) Notice: Subject to any disclaimer, the term of this patent is extended or adjusted under 35 U.S.C. 154(b) by 716 days.

(21) Appl. No.: 12/094,799

(22) PCT Filed: Nov. 28, 2006

(86) PCT No.: PCT/EP2006/068993
§ 371 (c)(1),
(2), (4) Date: May 23, 2008

(87) PCT Pub. No.: WO2007/060253
PCT Pub. Date: May 31, 2007

(65) Prior Publication Data
US 2008/0269322 A1 Oct. 30, 2008

(30) Foreign Application Priority Data
Nov. 28, 2005 (EP) .................... 05111394

(51) Int. Cl.
*A61K 31/343* (2006.01)
*C07D 493/04* (2006.01)
(52) U.S. Cl. ...................................... 514/470; 549/464
(58) Field of Classification Search .............. 514/470; 549/464
See application file for complete search history.

(56) References Cited

U.S. PATENT DOCUMENTS
2004/0039016 A1    2/2004  Ghosh et al.

FOREIGN PATENT DOCUMENTS

| WO | WO 96/22275 A1 | 7/1996 |
| WO | WO 99/33792 A2 | 7/1999 |
| WO | WO 99/33793 A2 | 7/1999 |
| WO | WO 99/33795 A1 | 7/1999 |
| WO | WO 99/33815 A1 | 7/1999 |
| WO | WO 99/67254 A2 | 12/1999 |
| WO | WO 03/049746 A2 | 6/2003 |
| WO | WO 03/090690 A2 | 11/2003 |

OTHER PUBLICATIONS

Augustijns, P., et al. "Drug Absorption Studies of Prodrug Esters using the Caco-2 Model: Evaluation of Ester Hydrolysis and Transepithelial Transport", International Journal of Pharmaceutics, vol. 166 (1998) pp. 45-53.
Chou and Talalay, "Quantitative Analysis of dose-Effect Relationships: The Combined Effects of Multiple Drugs or Enzyme Inhibitors", Advanced Enzyme Regulations, vol. 22 (1984) pp. 27-55.
Hertogs, K., et al. "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs", Antimicrobial Agents and Chemotherapy, vol. 42, No. 2 (1998) pp. 269-276.
Cross, L.C., et al., "Rules for the Nomenclature of Organic Chemistry Section E: Stereochemistry", Pure and Applied Chemistry, vol. 45, (1976), pp. 11-30.
Goodman and Gilman, "The Pharmacological Basis of therapeutics", Eighth Edition, Chapter 11, (1990) "Biotransformation of Drugs", pp. 13-15.
Meyer, S., et al., "TMC114, a Novel Human Immunodeficiency Virus Type 1 Protease Inhibitor Active against Protease Inhibitor-Resistant Viruses, Including a Broad Range of Clinical Isolates", Antimicrobial Agents and Chemotherapy, vol. 49, No. 6, (2005), pp. 2314-2321.
International Search Report mailed Feb. 26, 2007 for corresponding Application No. PCT/EP2006/068993.

*Primary Examiner* — Taofiq A Solola

(57) ABSTRACT

The present invention concerns substituted aminophenylsulfonamide compounds, their use as protease inhibitors, in particular as broad-spectrum HIV protease inhibitors, processes for their preparation as well as pharmaceutical compositions and diagnostic kits comprising them. The present invention also concerns combinations of the present substituted aminophenylsulfonamide compounds with another anti-retroviral agent. It further relates to their use in assays as reference compounds or as reagents.

9 Claims, No Drawings

SUBSTITUTED AMINOPHENYLSULFONAMIDE COMPOUNDS AS HIV PROTEASE INHIBITOR

CROSS REFERENCE TO RELATED APPLICATIONS

This application is the national stage of PCT Application No. PCT/EP2006/068993, filed Nov. 28, 2006, which claims priority from European Patent Application No. 05111394.2, filed Nov. 28, 2005, the entire disclosures of which are hereby incorporated in their entirely.

The present invention relates to substituted aminophenylsulfonamide compounds, their use as protease inhibitors, in particular as broad-spectrum HIV protease inhibitors, processes for their preparation as well as pharmaceutical compositions and diagnostic kits comprising them. The present invention also concerns combinations of the present substituted aminophenylsulfonamide compounds with another anti-retroviral agent. It further relates to their use in assays as reference compounds or as reagents.

The virus causing the acquired immunodeficiency syndrome (AIDS) is known by different names, including T-lymphocyte virus 111 (HTLV-III) or lymphadenopathy-associated virus (LAV) or AIDS-related virus (ARV) or human immunodeficiency virus (HIV). Up until now, two distinct families have been identified, i.e. HIV-1 and HIV-2. Hereinafter, HIV will be used to generically denote these viruses.

One of the critical pathways in a retroviral life cycle is the processing of polyprotein precursors by aspartic protease. For instance the HIV viral gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

HIV protease inhibitors (PIs) are commonly administered to AIDS patients in combination with other anti-HIV compounds such as, for instance nucleoside reverse transcriptase inhibitors (NRTIs), non-nucleoside reverse transcriptase inhibitors (NNRTIs), fusion inhibitors such as T-20 or other protease inhibitors. Despite the fact that these antiretrovirals are very useful, they have a common limitation, namely, the targeted enzymes in HIV are able to mutate in such a way that the known drugs become less effective, or even ineffective against these mutant HIV viruses. Or, in other words HIV creates an ever-increasing resistance against the available drugs.

Resistance of retroviruses, and in particular HIV, against inhibitors is a major cause of therapy failure. For instance, half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. Therefore, there is a need in the art for new compounds for retrovirus therapy, more particularly for AIDS therapy. The need in the art is particularly acute for compounds that are active not only on wild type HIV, but also on the increasingly more common resistant HIV.

Known antiretrovirals, often administered in a combination therapy regimen, will eventually cause resistance as stated above. This often may force the physician to boost the plasma levels of the active drugs in order for said antiretrovirals to regain effectivity against the mutated HIV. The consequence of which is a highly undesirable increase in pill burden. Boosting plasma levels may also lead to an increased risk of non-compliance with the prescribed therapy. Thus, it is not only important to have compounds showing activity for a wide range of HIV mutants, it is also important that there is little or no variance in the ratio between activity against mutant HIV virus and activity against wild type HIV virus (also defined as fold resistance or FR) over a broad range of mutant HIV strains. As such, a patient may remain on the same combination therapy regimen for a longer period of time since the chance that a mutant HIV virus will be sensitive to the active ingredients will be increased.

Finding compounds with a high potency on the wild type and on a wide variety of mutants is also of importance since the pill burden can be reduced if therapeutic levels are kept to a minimum. One way of reducing this pill burden is finding anti-HIV compounds with good bioavailability, i.e. a favourable pharmacokinetic and metabolic profile, such that the daily dose can be minimized and consequently also the number of pills to be taken.

Another important characteristic of a good anti-HIV compound is that plasma protein binding of the inhibitor has minimal or even no effect on its potency.

Hitherto several protease inhibitors are on the market or are being developed.

One of those protease inhibitors is called TMC 114 or darunavir, a new protease inhibitor under clinical investigation for the treatment of HIV-infections. Darunavir has the following chemical name: (3R,3aS,6aR)-hexahydrofuro[2,3-b]furan-3-yl N-[(1S,2R)-1-benzyl-2-hydroxy-3-(N1-isobutylsulfanilamido)propyl]carbamate and the following chemical structure:

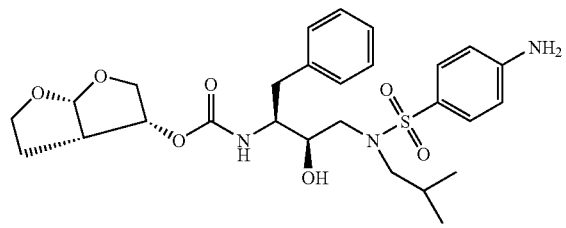

TMC114, a human immunodeficiency virus type 1 (HIV-1) protease inhibitor, is extremely potent against both wild-type (wt) and multidrug-resistant (MDR) viruses in vitro as well as in vivo. Although chemically resembling amprenavir (APV), the potency of TMC114 is substantially greater. It is designed to be active against HIV that is resistant to currently available protease inhibitors.

Although TMC114 has these excellent properties there is a constant high medical need for novel protease inhibitors that are able to combat a broad spectrum of mutants of HIV with little variance in fold resistance, have a good bioavailability and experience little or no effect on their potency due to plasma protein binding.

Surprisingly, the substituted aminophenylsulfonamide compounds of the present invention are found to have a favorable pharmacological and pharmacokinetic profile. Not only are they active against wild-type HIV but they also show a broad-spectrum activity against various mutant HIV exhibiting resistances against known protease inhibitors.

The present invention concerns substituted aminophenyl-sulfonamide compounds as protease inhibitors having the formula:

(I)

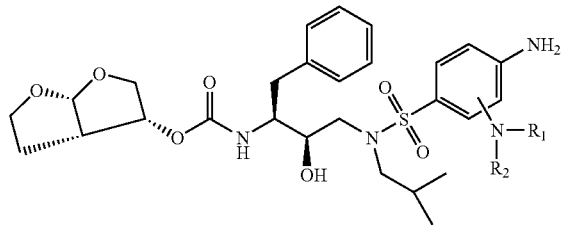

or N-oxide, salt, stereoisomeric form, racemic mixture, pro-drug, ester or metabolite thereof wherein $R_1$ and $R_2$ are, each independently, hydrogen, $C_{1-6}$-alkyl preferably $C_{1-4}$-alkyl optionally substituted by $C_{1-6}$ alkyloxy, hydroxyl, $C_{3-7}$ cycloalkyl, aryl, benzodioxolyl, $Het^1$, $Het^2$ or X wherein;

X is a carbon or nitrogen optionally substituted by —C(=O)—NH$_2$, $C_{1-6}$ alkyloxy-C(=O)— or $C_{1-6}$ alkyl-C(=O)—, Aryl as a group or part of a group is meant to include phenyl which may be optionally substituted with one or more substituents independently selected from $C_{1-6}$alkyl, $C_{1-6}$alkyloxy, amino$C_{1-6}$alkyl, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, $Het^1$, $Het^2$ optionally mono- or disubstituted aminocarbonyl, methylenedioxy, methylthio or methylsulfonyl, $Het^1$ as a group or part of a group is defined as a saturated or partially unsaturated monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl, $C_{1-6}$alkyloxy, amino$C_{1-6}$ alkyl, halogen, hydroxy, acetyl, oxo, optionally mono- or disubstituted amino, optionally mono- or disubstituted aminoalkyl, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic cycle or heterocycle having 3 to 14 ring members; and wherein $Het^2$ as a group or part of a group is defined as an aromatic monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl which may optionally substituted by $C_{3-7}$ cycloalkyl, $C_{1-6}$alkyloxy, amino-$C_{1-6}$ alkyl, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl, $Het^1$ and an aromatic monocyclic, bicyclic or tricyclic cycle or heterocycle having 3 to 12 ring members.

Interested compounds according to the invention are those compounds with structural formula (I) wherein $R_1$ is hydrogen and $R_2$ is $C_{1-6}$-alkyl preferably $C_{1-4}$-alkyl substituted by aryl which is substituted by halogen, or wherein said $C_{1-6}$-alkyl preferably $C_{1-4}$-alkyl is substituted by $Het^2$, or wherein said $C_{1-6}$-alkyl preferably $C_{1-4}$-alkyl is substituted by benzodioxolyl.

Preferred compounds are those of structural formula (I) wherein $R_1$ is hydrogen and $R_2$ is $C_{1-4}$-alkyl substituted by aryl, which is di-substituted by fluoride, or wherein said $C_{1-4}$alkyl is substituted by a saturated monocyclic heterocycle having 6 ring members containing nitrogen.

Most preferred are those compounds having the formula (II)

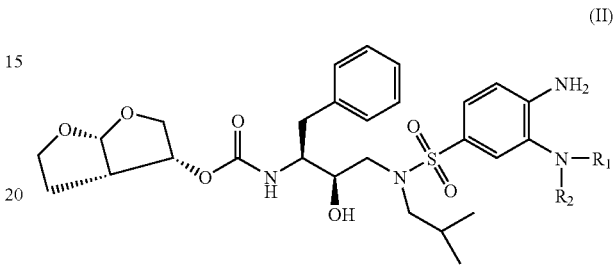

or N-oxide, salt, stereoisomeric form, racemic mixture, pro-drug, ester or metabolite thereof wherein $R_1$ and $R_2$ are, each independently, hydrogen, $C_{1-6}$-alkyl preferably $C_{1-4}$-alkyl optionally substituted by $C_{1-6}$ alkyloxy, hydroxyl, $O_{3-7}$ cycloalkyl, aryl, benzodioxolyl, $Het^1$, $Het^2$ or X wherein;

X is a carbon or nitrogen optionally substituted by —C(=O)—NH$_2$, $C_{1-6}$ alkyloxy-C(=O)— or $C_{1-6}$ alkyl-C(=O)—, Aryl as a group or part of a group is meant to include phenyl which may be optionally substituted with one or more substituents independently selected from $C_{1-6}$alkyl, $C_{1-6}$alkyloxy, amino$C_{1-6}$alkyl, halogen, hydroxy, optionally mono- or disubstituted amino, nitro, cyano, halo$C_{1-6}$ alkyl, carboxyl, $C_{1-6}$alkoxycarbonyl, $C_{3-7}$cycloalkyl, $Het^1$, $Het^2$ optionally mono- or disubstituted aminocarbonyl, methylenedioxy, methylthio or methylsulfonyl, $Het^1$ as a group or part of a group is defined as a saturated or partially unsaturated monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl, $C_{1-6}$alkyloxy, amino$C_{1-6}$ alkyl, halogen, hydroxy, acetyl, oxo, optionally mono- or disubstituted amino, optionally mono- or disubstituted aminoalkyl, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic cycle or heterocycle having 3 to 14 ring members; and wherein $Het^2$ as a group or part of a group is defined as an aromatic monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl which may optionally substituted by $C_{3-7}$ cycloalkyl, $C_{1-6}$alkyloxy, amino-$C_{1-6}$alkyl, halogen, hydroxy, optionally mono- or disubstituted amino, nitro, cyano, haloC$_{1-6}$alkyl, carboxyl, C$_{1-6}$alkoxycarbonyl, C$_{3-7}$cycloalkyl, optionally mono- or disubstituted aminocarbonyl, methylthio, methylsulfonyl, aryl, Het$^1$ and an aromatic monocyclic, bicyclic or tricyclic cycle or heterocycle having 3 to 12 ring members.

Of the compounds according to structural formula (II) the interested compounds are those wherein R$_1$ is hydrogen and R$_2$ is C$_{1-6}$-alkyl preferably C$_{1-4}$-alkyl substituted by aryl which is substituted by halogen, or wherein said C$_{1-6}$-alkyl preferably C$_{1-4}$-alkyl is substituted by Het$^2$, or wherein said C$_{1-6}$-alkyl preferably C$_{1-4}$-alkyl is substituted by benzodioxolyl.

Preferred are those compounds with structural formula (II) wherein R$_1$ is hydrogen and R$_2$ is C$_{1-4}$-alkyl substituted by aryl, which is di-substituted by fluoride, or wherein said C$_{1-4}$-alkyl is substituted by a saturated monocyclic heterocycle having 6 ring members containing nitrogen.

Most preferred are those compounds having the chemical name (3-{[4-amino-3-(2,4-difluoro-benzylamino)-benzenesulfonyl]-isobutyl-amino}-1-benzyl-2-hydroxy-propyl)-carbamic acid hexahydro-furo[2,3-b]furan-3-yl ester or [3-({4-amino-3-[(pyridin-2-ylmethyl)-amino]-benzenesulfonyl}-isobutylamino)-1-benzyl-2-hydroxy-propyl]-carbamic acid hexahydro-furo[2,3-b]furan-3-yl ester Furthermore, the present invention relates to pharmaceutical preparations, which as active constituents contain an effective dose of at least one of the compounds of formula (I or II) in addition to customary pharmaceutically innocuous excipients and auxiliaries. The pharmaceutical preparations normally contain 0.1 to 90% by weight of a compound of formula (I or II). The pharmaceutical preparations can be prepared in a manner known per se to one of skill in the art. For this purpose, at least one of a compound of formula (I or II), together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals, which contain a compound according to the invention, can be administered orally using e.g. including suspensions, capsules, tablets, sachets, solutions, suspensions, emulsions; parenterally using e.g. subcutaneous, intravenous, intramuscular, intrasternal injection or infusion techniques; rectally using e.g. suppositories; intravaginally; by inhalation, or topically. The preferred administration being dependent on the individual case e.g., the particular course of the disorder to be treated. Oral administration is preferred.

The person skilled in the art is familiar on the basis of his expert knowledge with the auxiliaries, which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds of formula (I) or (II) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I or II) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

Due to their favorable pharmacological properties, particularly their activity against multi-drug resistant HIV protease enzymes, the compounds of the present invention are useful in the treatment of individuals infected by HIV and for the prophylaxis of these individuals.

The prophylaxis treatment can be advantageous in cases where an individual has been subjected to a high risk of exposure to a virus, as can occur when individual has been in contact with an infected individual where there is a high risk of viral transmission. As an example, prophylactic administration of said compounds would be advantageous in a situation where a health care worker has been exposed to blood from an HIV-infected individual, or in other situations where an individual engaged in high-risk activities that potentially expose that individual to HIV.

In general, the compounds of the present invention may be useful in the treatment of warm-blooded animals infected with viruses whose existence is mediated by, or depends upon, the protease enzyme. Conditions which may be prevented or treated with the compounds of the present invention include, but is not limited to, treating a wide range of states of HIV infection: AIDS, ARC (Aids related complex), both symptomatic and asymptomatic, and actual or potential exposure to HIV. The compounds of the present are also useful for treating progressive generalized lymphadenophaty, Kaposi's syndrome, thrombocytopenia purpurea, AIDS-related neurological conditions such as AIDS dementia complex, multiple sclerosis, tropical parapesis, and also anti-HIV antibody positive and HIV-positive conditions, including such conditions in asymptomatic patients. For example, the compounds of this invention are useful in treating infection by HIV after suspected past exposure to HIV by e.g., blood transfusion, exchange of body fluids, bites, accidental needle stick, or exposure to patient blood during surgery. The term prevention includes prophylaxis of HIV infection and prophylaxis of the evolution of HIV infection to AIDS.

The compounds of the present invention or any derivative thereof may therefore be used as medicines against abovementioned conditions. Said use as a medicine or method of treatment comprises the systemic administration to HIV-infected subjects of an amount effective to combat the conditions associated with HIV and other pathogenic retroviruses, especially HIV-1. Consequently, the compounds of the present invention can be used in the manufacture of a medicament useful for treating conditions associated with HIV and other pathogenic retroviruses, in particular medicaments useful for treating patients infected with multi-drug resistant HIV virus.

In a preferred embodiment, the invention relates to the use of a compound of formula (I or II) or any derivative thereof in the manufacture of a medicament for treating or combating infection or disease associated with multi-drug resistant retrovirus infection in a mammal, in particular HIV-1 infection. Thus, the invention also relates to a method of treating a retroviral infection, or a disease associated with multi-drug resistant retrovirus infection comprising administering to a mammal in need thereof an effective amount of a compound of formula (I or II) or a derivative thereof.

In another preferred embodiment, the present invention relates to the use of formula (I or II) or any derivative thereof in the manufacture of a medicament for inhibiting a protease of a multi-drug resistant retrovirus in a mammal infected with said retrovirus, in particular HIV-1 retrovirus.

In another preferred embodiment, the present invention relates to the use of formula (I or II) or any derivative thereof in the manufacture of a medicament for inhibiting multi-drug resistant retroviral replication, in particular HIV-1 replication.

Also, the combination of an antiretroviral compound and a compound of the present invention can be used as a medicine. Thus, the present invention also relates to a product or composition containing (a) a compound of the present invention (according to formula (I or II)), and (b) another antiretroviral compound, as a combined preparation for simultaneous, separate or sequential use in treatment of retroviral infections, in particular, in the treatment of infections with multi-drug resistant retroviruses. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4, PRO-542, BMS-806; fusion inhibitors, such as, for example, T20, T1249, RPR 103611, YK-FH312, IC 9564, 5-helix, D-peptide ADS-J1; co-receptor binding inhibitors, such as, for example, AMD 3100, AMD-3465, AMD7049, AMD3451 (Bicyclams), TAK220, TAK 779, T-22, ALX40-4C; SHC-C (SCH351125), SHC-D, PRO-140, RPR103611, AK-602; RT inhibitors, such as, for example, foscarnet and prodrugs; nucleoside RTIs, such as, for example, AZT, 3TC, DDC, DD1, D4T, Abacavir, FTC, DAPD (Amdoxovir), dOTC (BCH-10652), fozivudine, DPC 817; nucleotide RTIs, such as, for example, PMEA, PMPA (tenofovir); NNRTIs, such as, for example, nevirapine, delavirdine, efavirenz, 8 and 9-CI TIBO (tivirapine), loviride, TMC-125, dapivirine, MKC-442, UC 781, UC 782, Capravirine, QM96521, GW420867X, GW-3011, GW-4511, GW-4751, DPC 961, DPC963, DPC082, DPC083, calanolide A, SJ-3366, TSAO, 4"-deaminated TSAO, MV150, MV026048, PNU-142721; RNAse H inhibitors, such as, for example, SP1093V, PD126338; TAT inhibitors, such as, for example, RO-5-3335, K12, K37; integrase inhibitors, such as, for example, L 708906, L 731988, S-1360; protease inhibitors, such as, for example, amprenavir and prodrug GW908, ritonavir, nelfinavir, saquinavir, indinavir, lopinavir, palinavir, BMS186316, atazanavir, DPC 681, DPC 684, tipranavir, AG1776, mozenavir, DMP-323, GS3333, KNI-413, KNI-272, L754394, L756425, LG-71350, PD161374, PD173606, PD177298, PD178390, PD178392, PNU 140135, TMC-114, maslinic acid, U-140690, RO-033-4649; glycosylation inhibitors, such as, for example, castanospermine, deoxynojirimycine.

The compounds of the present invention may also be administered in combination with modulators of the metabolization following application of the drug to an individual. These modulators include compounds that interfere with the metabolization at cyto-chromes, such as cytochrome P450. Some modulators inhibit cytochrome P450. It is known that several isoenzymes exist of cytochrome P450, one of which is cytochrome P450 3A4. Ritonavir is an example of a modulator of metabolization via cytochrome P450. Interesting compounds having an effect at cytochrome P450 include those compounds containing a thiazolyl, imidazolyl or pyridinyl moiety. Such combination therapy in different formulations may be administered simultaneously, separately or sequentially. Alternatively, such combination may be administered as a single formulation, whereby the active ingredients are released from the formulation simultaneously or separately.

Such modulator may be administered at the same or different ratio as the compound of the present invention. Preferably, the weight ratio of such modulator vis-à-vis the compound of the present invention (modulator: compound of the present invention) is 1:1 or lower, more preferable the ratio is 1:3 or lower, suitably the ratio is 1:10 or lower, more suitably the ratio is 1:30 or lower.

The combination may provide a synergistic effect, whereby viral infectivity and its associated symptoms may be prevented, substantially reduced, or eliminated completely. Combinations of the compounds of formula (I or II) with another HIV protease inhibitor as cytochrome $P_{450}$ inhibitor can act synergistically, in an additive way or antagonistically. This can be assessed in an experimental setting where the potency of different ratios of the two HIV-protease inhibitors is measured. Results can be plotted in an isobologram graph according to the method described by Chou and Talalay (Adv. Enzyme Regul. 22: 27-55, 1984) Synergism between two inhibitors would mean a more potent combination therapy, but with no increase in undesired side effects.

Another aspect of the present invention concerns a kit or container comprising a compound of formula (I or II) in an amount effective for use as a standard or reagent in a test or assay for determining the ability of a potential pharmaceutical to inhibit HIV protease, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram™. The Antivirogram™ is a highly automated, high throughput, second generation, recombinant assay that can measure susceptibility, especially viral susceptibility, to the compounds of the present invention. (Hertogs K, de Bethune M P, Miller V et al. *Antimicrob Agents Chemother,* 1998; 42(2):269-276)

Whenever the term "substituted" is used in defining the compounds of formula (I or II), it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein, the term "halo" or "halogen" as a group or part of a group is generic for fluoro, chloro, bromo or iodo.

The term "$C_{1-4}$alkyl" as a group or part of a group defines straight and branched chained saturated hydrocarbon radicals having from 1 to 4 carbon atoms, such as, for example, methyl, ethyl, propyl, butyl and 2-methyl-propyl, the like.

The term "$C_{1-6}$alkyl" as a group or part of a group defines straight and branched chained saturated hydrocarbon radicals having from 1 to 6 carbon atoms such as the groups defined for $C_{1-4}$alkyl and pentyl, hexyl, 2-methylbutyl, 3-methylpentyl and the like.

The term "$C_{3-7}$cycloalkyl" as a group or part of a group is generic to cyclopropyl, cyclobutyl, cyclopentyl, cyclohexyl or cycloheptyl.

As used herein, the term (=O) forms a carbonyl moiety with the carbon atom to which it is attached.

As used herein before, the term "one or more" covers the possibility of all the available C-atoms, where appropriate, to be substituted, preferably, one, two or three.

When any variable (e.g. halogen or $C_{1-4}$alkyl) occurs more than one time in any constituent, each definition is independent.

Lines drawn from substituents into ring systems indicate that the bond may be attached to any of the suitable ring atoms.

Aryl as a group or part of a group is meant to include phenyl which may be optionally substituted with one or more substituents independently selected from $C_{1-6}$alkyl, $C_{1-6}$alkyloxy, amino$C_{1-6}$alkyl, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, Het$^2$ optionally mono- or disubstituted aminocarbonyl, methylenedioxy, methylthio or methylsulfonyl.

Het$^1$ as a group or part of a group is defined as a saturated or partially unsaturated monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl, $C_{1-6}$alkyloxy, amino$C_{1-6}$alkyl, halogen, hydroxy, acetyl, oxo, optionally mono- or disubstituted amino, optionally mono- or disubstituted aminoalkyl, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic cycle or heterocycle having 3 to 14 ring members.

Het$^2$ as a group or part of a group is defined as an aromatic monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl which may optionally substituted by $C_{3-7}$cycloalkyl, $C_{1-6}$alkyloxy, amino$C_{1-6}$alkyl, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl, Het$^1$ and an aromatic monocyclic, bicyclic or tricyclic cycle or heterocycle having 3 to 12 ring members.

The salts of compounds of formula (I) or (II) are those wherein the counter ion is pharmaceutically or physiologically acceptable. However, salts having a pharmaceutically unacceptable counter ion may also find use, for example, in the preparation or purification of a pharmaceutically acceptable compound of formula (I) or (II). All salts, whether pharmaceutically acceptable or not are included within the ambit of the present invention.

The pharmaceutically acceptable or physiologically tolerable addition salt forms, which the compounds used in the present invention are able to form, can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of formula (I) or (II) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms, which the compounds of the present invention are able to form. Examples of such forms are e.g. hydrates, alcoholates and the like.

The present compounds used in the present invention may also exist in their N-oxide forms of formula (I) or (II) wherein one or several nitrogen atoms are oxidized to the so-called N-oxide. To obtain said N-oxides the compounds of formula (I or II) may be converted to the corresponding N-oxide forms following art-known procedures for converting a trivalent nitrogen into its N-oxide form. Said N-oxidation reaction may generally be carried out by reacting the starting material of formula (I or II) with appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chloro-benzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The present compounds used in the invention may also exist in their tautomeric forms. Such forms, although not explicitly indicated in the above formula are intended to be included within the scope of the present invention.

The present compound used in the current invention may also exist in their stereochemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereochemically isomeric forms, which said compounds might possess.

Said mixture may contain all diastereomers and/or enantiomers of the basic molecular structure of said compound. All stereochemically isomeric forms of the compounds used in the present invention either in pure form or in admixture with each other are embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I or II) can be obtained separately by conventional methods. Appropriate physical separation methods, which may advantageously be employed, are for example selective crystallization and chromatography, e.g. column chromatography.

It is clear to a person skilled in the art that compounds of formula (I) or (II) contains five asymmetric centers and thus may exist as different stereoisomeric forms. Two asymmetric centers are indicated with an asterisk (*) in the figure below for formula (I)

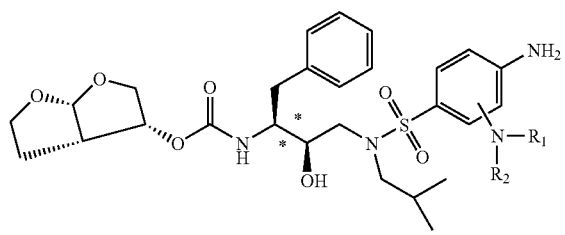

(I)

The absolute configuration of each asymmetric center that may be present in the compounds of formula (I) may be indicated by the stereochemical descriptors R and S, this R and S notation corresponding to the rules described in Pure Appl. Chem. 1976, 45, 11-30. The same is applicable to formula (II).

The compounds and drugs as disclosed herein can, if desired, be in the form of a so-called prodrug. "Prodrug" means the pharmacologically acceptable derivatives such as esters, amides and phosphates, such that the resulting in vivo biotransformation product of the derivative is the active compound as defined in formula (I) or (II) or drug concerned. The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs of a compound used in the present invention are prepared by modifying functional groups present in the compound in such a way that the modifications are cleaved, either in routine manipulation or in vivo, to the parent compound. Prodrugs include compounds used in the present invention wherein a hydroxy group, for instance the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795, WO 99/33815, WO 99/33793, WO 99/33792 and WO 03/090690 all incorporated herein by reference.

Prodrugs are characterized by improved aqueous solubility relative to the parent compounds, increased bioavailability and are readily metabolized into the active inhibitors in vivo.

EXAMPLE SECTION

General Experimental Procedures.

NMR spectra were recorded on a Bruker AC-300 or Bruker Avance 400 spectrometer, operating at 300 or 400 MHz for $^1$H with $CDCl_3$ as solvent. In every case tetramethyl-silane (TMS) was used as internal standard. Chemical shifts are given in ppm.

Multiplicity is indicated using the following abbreviations: d for doublet, t for a triplet, m for a multiplet, etc. For the sake of brevity it was opted to completely characterize (NMR included) two representative examples of each subset of compounds. Low-resolution mass spectra (LRMS) were performed on a single quadrupole (Waters ZMD, Shimadzu QP8000a or Agilent 1100-SL), ion trap (ThermoFinnigan LCQ Deca) or a time of flight (Waters LCT) mass spectrometer using electrospray ionization (ESI) in positive mode. All reagents, were purchased from commercial sources (Acros, Aldrich, Fluorochem, . . . ) and were used as received. Column chromatography was carried out on silica gel 60 Å, 60-200 µm (ROCC). Thin layer chromatography was performed on silica gel 60 $F_{254}$ plates (Merck). Analytical HPLC was done on a Waters Alliance 2690 (pump+auto sampler) system equipped with a Waters 996 photo diode array-detector (system 1) or an Agilent 100-SL system equipped with an Agilent G1316A diode array-detector (system 2) or a Shimadzu QP8000a system with a Shimadzu SPD-M10A diode array-detector (system 3). To check the purity of the end products one chromatographic system of the 3 different systems was used. System 1: column: Waters Xterra MS C18, (3.5 μm, 4.60 mm×100 mm), mobile phase A: 10 mM CH₃COONH₄ in H₂O, mobile phase B: CH₃CN. Analysis were run at 30° C. using a flow rate of 1 mL/min applying the following gradient: 0 min: 5% B, 10 min: 95% B, 12 min: 95% B. In every case, 10 μl of a 1 mM solution was injected. The equilibration time between two runs was 3 minutes. Eluted peaks were detected at a single wavelength ($\lambda_{max}$). System 2: column: Zorbax® Extend-C18, (3.5 μm, 4.60 mm×150 mm), mobile phase A: CH₃CN, mobile phase B: 10 mM NH₃ in H₂O. Analysis were run at 35° C. using a flow rate of 1 mL/min applying the following gradient: 0 min: 2% A, 10 min: 98% A, 15 min: 98% A. Eluted peaks were detected at a UV range between 220-320 nm. System 3: column Alltech Prefail C18, (3.0 μm, 4.60 mm×50 mm), mobile phase A: 10 mM HCOOH in CH₃CN, mobile phase B: 10 mM HCOOH in H₂O. Analysis were run at 50° C. using a flow rate of 4 mL/min applying the following gradient: 0 min: 100% B, 8 min: 0% B, 10 min: 0% B. Eluted peaks were detected at a UV range between 250-350 nm. The retention time is given and is reported in minutes. The synthesis of one compound is fully described. The other compounds were synthesized in the same way as already described. All compounds were identified by LRMS.

Scheme 1. Synthesis of {1-Benzyl-3-[(3,4-diamino-benzenesulfonyl)-isobutyl-amino]-2-hydroxy-propyl}-carbamic acid hexahydro-furo[2,3-b]furan-3-yl ester derivatives (78-138)

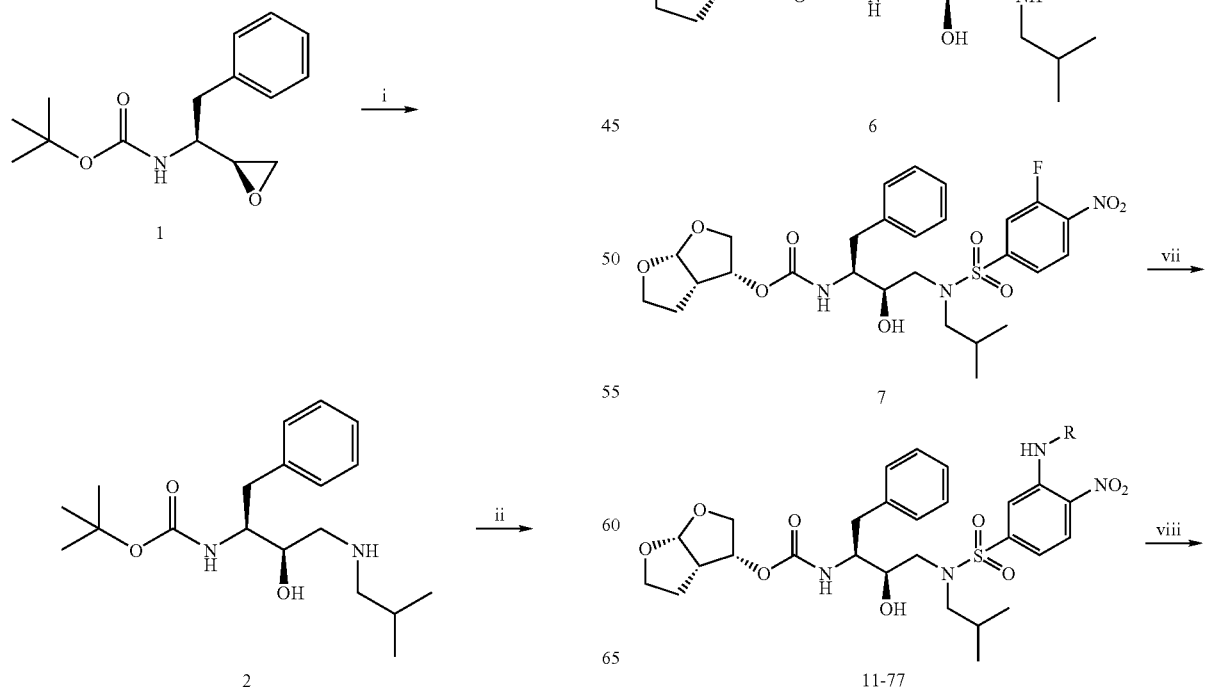

-continued

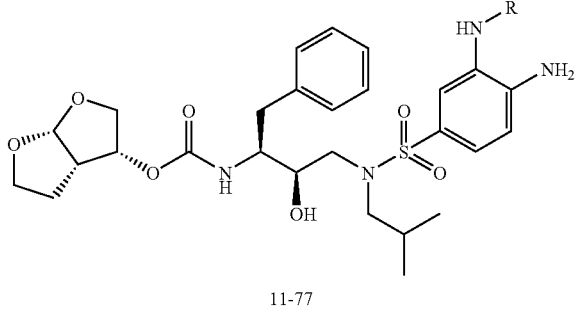

11-77

(i) Isobutylamine, $CH_2Cl_2$; (ii) benzylchloroformate, $Et_3N$, $CH_2Cl_2$; (iii) HCl/i-PrOH, $CH_3OH$; (iv) carbonic acid 2,5-dioxo-pyrrolidin-1-yl ester hexahydro-furo[2,3-b]furan-3-yl ester, $Et_3N$, $CH_2Cl_2$; (v) Pd/C, $H_2$, $CH_3OH$; (vi) 3-fluoro-4-nitro-benzenesulfonyl chloride, sat. $NaHCO_3$/$H_2O$, $CH_2Cl_2$; (vii) $RNH_2$, DIPEA, THF/1-PrOH/$H_2O$; (viii) Pd/C, $NH_4^+HCOO^-$, 2-methyl-tetrahydro-furan.

Description of the Chemical Reactions for Scheme 1

(1-Benzyl-2-hydroxy-3-isobutylamino-propyl)-carbamic acid tert-butyl ester (2) This compound was synthesized from the commercially available (1-oxiranyl-2-phenyl-ethyl)-carbamic acid tert-butyl ester (1), which was reacted with isobutylamine thereby forming the amino alcohol 2.

Ng, J. S.; Przybyla, C. A.; Zhang, S. Method of preparing retroviral protease inhibitor intermediates via diastereromer purification. PCT Int. Appl. 1996, WO 9622275.

(3-tert-Butoxycarbonylamino-2-hydroxy-4-phenyl-butyl)-isobutyl-carbamic acid benzyl ester (3)

(1-Benzyl-2-hydroxy-3-isobutylamino-propyl)-carbamic acid tert-butyl ester (2) (24.50 g, 72.80 mmol, 1 equiv) and triethylamine (7.37 g, 72.80 mmol, 1 equiv) were dissolved in dichloromethane (500 mL). The solution was cooled to −1.5° C., followed by the dropwise addition of benzylchloroformate (12.40 g, 72.80 mmol, 1 equiv). The solution was stirred at 0° C. for 24 h. Due to the incompleteness of the reaction, benzylchloroformate (2.40 g, 14.07 mmol) and triethylamine (1.44 g, 14.23 mmol) were added to the solution. The solution was stirred at room temperature for 24 h. The solution was diluted with 2% $Na_2CO_3$ solution (300 mL) and the mixture was stirred for 10 min. The organic layer was separated, washed with water (2×) and saturated sodium chloride solution (1×). The organic layer was dried on $MgSO_4$, filtered, and evaporated to dryness to obtain the desired product as a yellow colored oil (34.30 g, 72.80 mmol, quantitative). LRMS (ES+): m/z 471 [M+H]$^+$.

1-Benzyl-3-(benzyloxycarbonyl-isobutyl-amino)-2-hydroxy-propyl-ammonium chloride (4)

(3-tert-Butoxycarbonylamino-2-hydroxy-4-phenyl-butyl)-isobutyl-carbamic acid benzyl ester (3) (34.30 g, 72.90 mmol, 1 equiv) was dissolved in methanol (170 mL), followed by the addition of 5-6 N HCl in isopropanol (75 mL). The solution was stirred at room temperature for 64 h. Volatiles were evaporated under reduced pressure. The crude product was coevaporated with ethyl acetate (150 mL) to obtain 4 as a white solid (29.70 g, 72.90 mmol, quantitative). LRMS (ES+): m/z 371 [M+H]$^+$.

[1-Benzyl-3-(benzyloxycarbonyl-isobutyl-amino)-2-hydroxy-propyl]-carbamic acid hexahydro-furo[2,3-b]furan-3-yl ester (5)

A solution of 1-benzyl-3-(benzyloxycarbonyl-isobutyl-amino)-2-hydroxy-propyl-ammonium chloride (4) (29.70 g, 72.90 mmol, 1 equiv), triethylamine (22.00 g, 220 mmol, 3 equiv) and carbonic acid 2,5-dioxo-pyrrolidin-1-yl ester hexahydro-furo[2,3-b]furan-3-yl ester (19.80 g, 73.00 mmol, 1 equiv) in 120 mL of dichlomethane were stirred at ambient temperature. Due to the incompleteness of the reaction, carbonic acid 2,5-dioxo-pyrrolidin-1-yl ester hexahydro-furo[2,3-b]furan-3-yl ester (5.00 g, 18.43 mmol) was added to the solution. The solution was stirred at room temperature for 24 h. The solution was washed twice with 300 mL of water and once with 300 mL of saturated $NaHCO_3$ solution. The organic layer was dried on $MgSO_4$, filtered, and evaporated to dryness to obtain the desired product as a white solid. (37.04 g, 70.34 mmol, 96.4%). LRMS (ES+): m/z 527 [M+H]$^+$.

(1-Benzyl-2-hydroxy-3-isobutylamino-propyl)-carbamic acid hexahydro-furo[2,3-b]furan-3-yl ester (6)

After displacing the air with $N_2$, palladium on charcoal (10%, 5.00 g, 47.00 mmol, 0.32 equiv) was added followed by the addition of a solution of [1-benzyl-3-(benzyloxy-carbonyl-isobutyl-amino)-2-hydroxy-propyl]-carbamic acid hexahydro-furo[2,3-b]furan-3-yl ester (78.36 g, 148.80 mmol, 1 equiv) in tetrahydrofurane. For a few minutes vacuum was applied and replaced by $H_2$. After stirring for 24 h at room temperature. $N_2$ was then introduced in the flask to displace the remaining $H_2$. The palladium catalyst was removed by filtration over a bed of dicalite under $N_2$ and the filter was washed with tetrahydrofurane. The filtrate was evaporated under reduced pressure. (58.40 g, 148.80 mmol, quantitative). LRMS (ES+): m/z 393 [M+H]$^+$; $^1$H-NMR (CDCl$_3$) δ0.91 (d, 3H, $CH_3$), 0.93 (d, 3H, $CH_3$), 1.45-1.57 (m, 2H, $CH_2$, H4), 1.58-1.83 (m, 1H, CH (isobutyl)), 2.43 (dd, 2H, $CH_2$—N (isobutyl)), 2.66-2.81 (m, 3H, $CH_2$—N and CH of $CH_2C_6H_5$), 2.87-2.96 (m, 1H, CH, H3a), 3.06 (dd, 1H, CH of $CH_2C_6H_5$), 3.51-3.57 (m, 1H, $CH_2$, H5), 3.67-3.75 (m, 2H, CH and $CH_2$, H2), 3.81-3.93 (m, 2H, CH—OH and $CH_2$, H5), 3.94-4.00 (m, 1H, $CH_2$, H2), 5.01-5.08 (m, 1H, CH, H3), 5.10 (d, 1H, NH), 5.64 (d, 1H, CH, H6a), 7.16-7.31 (m, 5H, $C_6H_5$).

{1-Benzyl-3-[(3-fluoro-4-nitro-benzenesulfonyl)-isobutyl-amino]-2-hydroxy-propyl}-carbamic acid hexahydro-furo[2,3-b]furan-3-yl ester (7)

(1-Benzyl-2-hydroxy-3-isobutylamino-propyl)-carbamic acid hexahydro-furo[2,3-b]-furan-3-yl ester (6) (9.81 g, 25 mmol, 1 equiv) was dissolved in dichloromethane (100 mL), followed by the addition of saturated $NaHCO_3$ solution (100 mL). A solution of 3-fluoro-4-nitro-benzenesulfonyl chloride (6.11 g, 25.50 mmol, 1.02 equiv) in dichloro-methane (100 mL) was added drop wise to the previous solution. The solution was vigorously stirred at 20° C. After stirring for 4 h, the organic layer was separated and washed with saturated $NaHCO_3$ solution (100 mL), water (100 mL), 5% HCl solution (100 mL) and brine (100 mL). The organic layer was dried on $MgSO_4$, filtered, and evaporated to dryness. The crude product was recrystallized from 2-propanol (550 mL) (9.58 g, 25 mmol, 64.30%). LRMS (ES+): m/z 596 [M+H]$^+$; $^1$H-NMR (CDCl$_3$) δ0.90 (d, 3H, $CH_3$), 0.92 (d, 3H, $CH_3$), 1.40-1.72 (m, 2H, $CH_2$, H4), 1.80-1.92 (m, 1H, CH (isobutyl)), 2.79 (dd, 1H, $CH_2$—N), 2.87-3.19 (m, 5H, $CH_2$—N (isobutyl), CH, H3, $CH_2$—N and CH of $CH_2C_6H_5$), 3.19-3.29 (m, 1H, CH of $CH_2C_6H_5$), 3.29-3.39 (brs, 1H, OH), 3.60-3.78 (m, 2H, $CH_2$, H5 and H2), 3.78-3.90 (m, 3H, CH, H5, CH—OH and CH), 3.95 (dd, 1H, $CH_2$, H2), 4.90 (d, 1H, NH), 4.98-5.10 (m, 1H, CH, H3), 5.66 (d, 1H, CH, H6a), 7.19-7.33 (m, 5H, C$_6$H$_5$), 7.68-7.74 (m, 2H, CH of C$_6$H$_3$FNO$_2$), 8.15-8.20 (m, 1H, CH of C$_6$H$_3$FNO$_2$).

(1-Benzyl-3-{[3-(2,4-difluoro-benzylamino)-4-nitro-benzenesulfonyl]-isobutyl-amino}-2-hydroxy-propyl)-carbamic acid hexahydro-furo[2,3-b]furan-3-yl ester (11)

{1-Benzyl-3-[(3-fluoro-4-nitro-benzenesulfonyl)-isobutyl-amino]-2-hydroxy-propyl}-carbamic acid hexahydro-furo[2,3-b]furan-3-yl ester (7) (0.40 g, 0.67 mmol, 1 equiv) and 2,4-difluoro-benzylamine (0.14 g, 1 mmol, 1.49 equiv) were dissolved in tetrahydrofurane (10 mL). The solution was heated to reflux for 18 h. The solution was concentrated and the crude product was dissolved in dichloromethane (15 mL). The organic layer was washed with saturated NaHCO$_3$ solution (15 mL). The organic layer was separated and evaporated under reduced pressure to yield the title compound (0.48 g, 0.67 mmol, quantitative). LRMS (ES+): m/z 719 [M+H]$^+$.

Example 1 benzenesulfon-yl]-isobutyl-amino}-1-benzyl-2-hydroxy-propyl)-carbamic acid hexahydro-furo[2,3-b]furan-3-yl ester (78)

(1-Benzyl-3-{[3-(2,4-difluoro-benzylamino)-4-nitro-benzenesulfonyl]-isobutyl-amino}-2-hydroxy-propyl)-carbamic acid hexahydro-furo[2,3-b]furan-3-yl ester (11) (0.10 g, 0.14 mmol, 1 equiv), palladium on charcoal (10%, 0.45 g, 0.42 mmol, 3 equiv), and ammonium formiate (0.050 g, 0.84 mmol, 6 equiv) were suspended in methanol (1 mL). The solution was heated to reflux for 4 min. The catalyst was filtered over a bed of celite and the filtrate was evaporated to dryness. The crude product was partitioned between dichloromethane and water. The organic layer was separated, dried on MgSO4, filtered and evaporated under reduced pressure (0.10 g, 0.14 mmol, 100%). LRMS (ES+): m/z 689 [M+H]$^+$; HPLC (system 3) t$_R$ 9.65 min, 95%; $^1$H-NMR (CDCl$_3$) δ0.87 (d, 3H, CH$_3$), 0.93 (d, 3H, CH$_3$), 1.39-1.51 (m, 1H, CH$_2$, H4), 1.59-1.70 (m, 1H, CH$_2$, H4), 1.70-1.90 (m, 1H, CH (isobutyl)), 2.65 (dd, 1H, CH$_2$—N), 2.71-2.98 (m, 4H, CH$_2$—N (isobutyl), CH$_2$—N, CH, H3a), 3.02 (d, 1H, CH of CH$_2$C$_6$H$_5$), 3.08 (d, 1H, CH of CH$_2$C$_6$H$_5$), 3.57-3.78 (m, 3H, CH, CH, H2 and CH, H5), 3.78-4.00 (m, 3H, CH—OH, CH, H2 and CH, H5), 4.37 (d, 2H, CH$_2$ of CH$_2$C$_6$H$_5$), 4.85 (d, 1H, NH), 4.92-5.07 (m, 1H, H3), 5.62 (d, 1H, CH, H6a), 6.75 (d, 1H, CHarom), 6.78-6.90 (m, 2H, CHarom (2×)), 6.94-7.03 (m, 1H, CHarom), 7.07-7.32 (m, 11H, CHarom (11×)).

Example 2

Preparation of [3-({4-amino-3-[(pyridin-2-ylmethyl)-amino]-benzenesulfonyl}-isobutyl-amino)-1-benzyl-2-hydroxy-propyl]-carbamic acid hexahydro-furo[2,3-b]furan-3-yl ester (80)

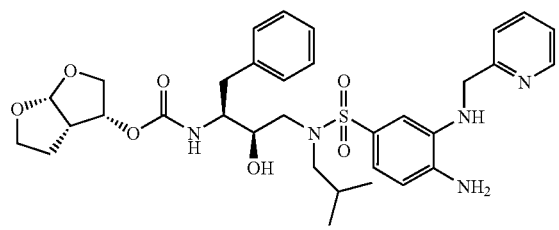

LRMS (ES+): m/z 655 [M+H]$^+$; HPLC (system 3) t$_R$ 8.39 min, 94%; $^1$H-NMR (CDCl$_3$) δ 0.70 (d, 3H, CH$_3$), 0.78 (d, 3H, CH$_3$), 1.15-1.28 (m, 1H, CH$_2$, H4), 1.28-1.49 (m, 1H, CH$_2$, H4), 1.69-1.92 (m, 1H, CH (isobutyl)), 2.32 (dd, 1H, CH$_2$—N (isobutyl)), 2.40-2.58 (m, 2H, CH$_2$—N (isobutyl) and CH, H3a), 2.60-2.82 (m, 2H, CH$_2$, CH$_2$—N), 3.00 (d, 1H, CH of C$_6$H$_2$C$_6$H$_5$), 3.19 (d, 1H, CH of CH$_2$C$_6$H$_5$), 3.25-3.42 (m, 1H, CH, H5), 3.42-3.65 (m, 3H, CH—OH, CH, and CH, H2), 3.65-3.78 (m, 1H, CH, H5), 3.78-3.91 (m, 1H, CH, H2), 4.40 (s, 2H, CH$_2$ of CH$_2$C$_5$H$_4$N), 4.72-4.85 (m, 1H, CH, H3), 4.90 (d, 1H, NH), 5.48 (d, 1H, CH, H6a), 5.55-5.78 (m, 1H, NH), 6.48-6.65 (m, 2H, CHarom (2×)), 6.80 (d, 1H, CHarom), 7.01-7.15 (m, 1H, CHarom), 7.15-7.29 (m, 5H, CHarom (5×)), 7.30 (d, 1H, CHarom), 7.62-7.80 (m, 1H, CHarom), 8.50 (d, 1H, CHarom).

Table 1

Table I represents some compounds with R$^1$ and R$^2$ substituents, according to formula (I), which were synthesized using above-mentioned processes.

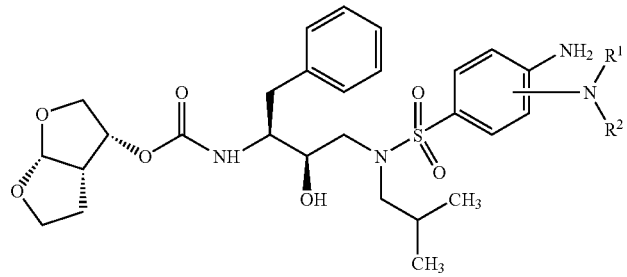

| Compound No | R$^1$ | R$^2$ | Mol Weight | ES+ | Mol Formula |
|---|---|---|---|---|---|
| 78 | H | (2,4-difluorobenzyl) | 688,791 | 689 | C34H42F2N4O7S |

-continued
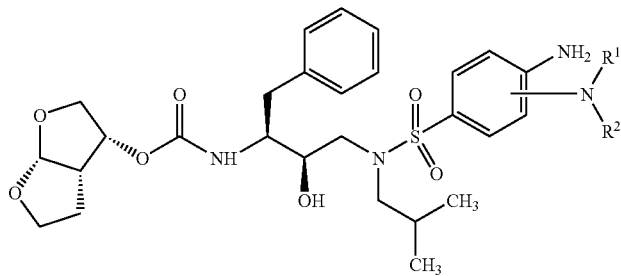
| Compound No | R¹ | R² | Mol Weight | ES+ | Mol Formula |
|---|---|---|---|---|---|
| 80 | H | 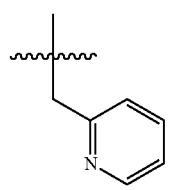 | 653,799 | 654 | C33H43N5O7S |
| 81 | H | 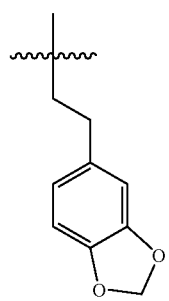 | 710,847 | 711 | C36H46N4O9S |
| 82 | H | 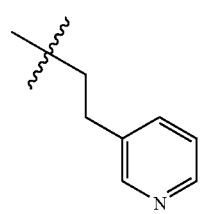 | 667,826 | 668 | C34H45N5O7S |
| 84 | H | 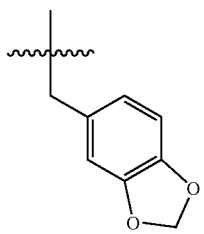 | 696,82 | 697 | C35H44N4O9S |
| 85 | H | 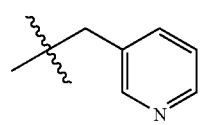 | 653,799 | 654 | C33H43N5O7S |

-continued
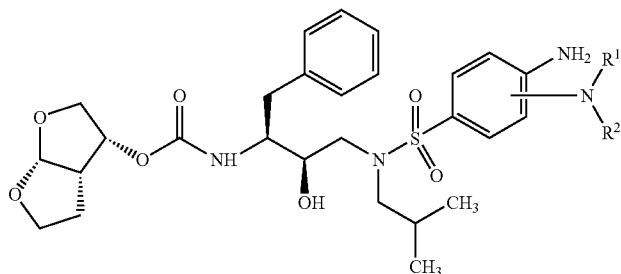
| Compound No | R¹ | R² | Mol Weight | ES+ | Mol Formula |
|---|---|---|---|---|---|
| 86 | H | morpholinopropyl | 675,846 | 676 | C33H49N5O8S |
| 87 | H | piperidinopropyl | 673,874 | 674 | C34H51N5O7S |
| 88 | H | 4-acetylpiperazinylpropyl | 716,899 | 717 | C35H52N6O8S |
| 89 | H | imidazolylpropyl | 670,83 | 671 | C33H46N6O7S |
| 91 | H | 3-fluorobenzyl | 670,801 | 671 | C34H43FN4O7S |
| 92 | H | 4-pyridylmethyl | 653,799 | 654 | C33H43N5O7S |
| 94 | H | —(CH$_2$)$_3$—OH | 620,766 | 621 | C30H44N4O8S |
| 95 | H | thiazolylmethyl | 659,825 | 660 | C31H41N5O7S2 |

-continued
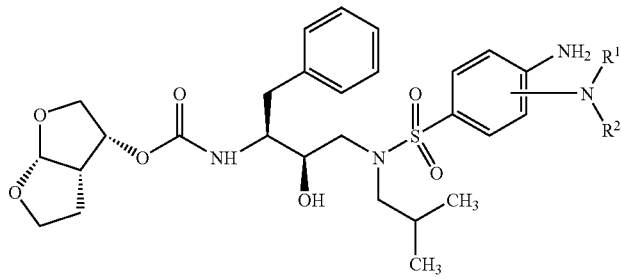
| Compound No | R¹ | R² | Mol Weight | ES+ | Mol Formula |
|---|---|---|---|---|---|
| 96 | H | (CH₂-tetrahydrofuran-2-yl) | 646,804 | 647 | C32H46N4O8S |
| 97 | H | —(CH₂)₂—OH | 606,739 | 607 | C29H42N4O8S |
| 98 | H | (CH₂-(2-ethylphenoxy)) | 682,837 | 683 | C35H46N4O8S |
| 100 | H | (CH₂-furan-2-yl) | 642,772 | 643 | C32H42N4O8S |
| 101 | H | (CH₂-cyclohexyl) | 658,859 | 659 | C34H50N4O7S |
| 102 | H | (CH₂CH₂-(1H-imidazol-4-yl)) | 656,803 | 657 | C32H44N6O7S |
| 103 | H | (CH₂CH₂CH₂-(1-isobutyl-1H-imidazol-5-yl)) | 712,911 | 713 | C36H52N6O7S |

-continued
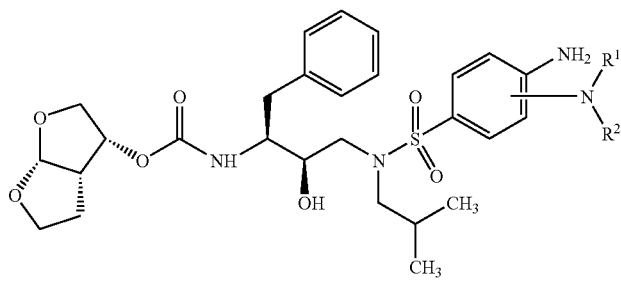
| Compound No | R¹ | R² | Mol Weight | ES+ | Mol Formula |
|---|---|---|---|---|---|
| 105 | H | (4-methoxypiperidin-1-yl)propyl | 703,9 | 704 | C35H53N5O8S |
| 106 | H | (pyrrolidin-1-yl)butyl | 673,874 | 674 | C34H51N5O7S |
| 107 | H | (Boc-amino)propyl | 705,872 | 706 | C34H51N5O9S |
| 109 | H | CH₃ | 576,713 | 577 | C28H40N4O7S |
| 113 | H | (pyrrolidin-1-yl)propyl | 659,847 | 660 | C33H49N5O7S |
| 114 | H | benzyl | 652,811 | 653 | C34H44N4O7S |

-continued
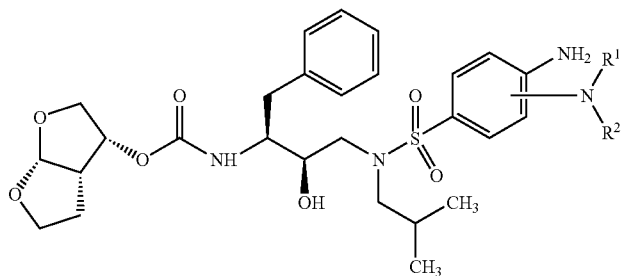
| Compound No | R¹ | R² | Mol Weight | ES+ | Mol Formula |
|---|---|---|---|---|---|
| 115 | H | ![imidazole-cyclohexylmethyl] | 752,976 | 753 | C39H56N6O7S |
| 118 | H | ![N-ethylpyrrolidine] | 673,874 | 674 | C34H51N5O7S |
| 119 | H | ![isobutyl] | 618,794 | 619 | C31H46N4O7S |
| 121 | CH₃ | CH₃ | 590,74 | 591 | C29H42N4O7S |
| 125 | CH₃ | ![benzyl] | 666,838 | 667 | C35H46N4O7S |
| 126 | H | ![N-ethylpyrrolidine] | 673,874 | 674 | C34H51N5O7S |
| 134 | H | ![Boc-piperidine] | 759,964 | 760 | C38H57N5O9S |

-continued

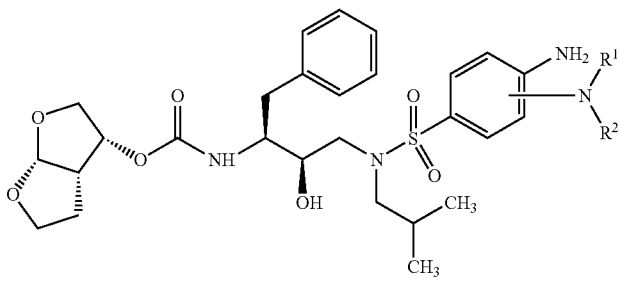

| Compound No | R¹ | R² | Mol Weight | ES+ | Mol Formula |
|---|---|---|---|---|---|
| 135 | H | ~~CH₂CH₂OCH₃ | 620,766 | 621 | C30H44N4O8S |
| 137 | H | ~~(CH₂)₃-N-pyrrolidinone | 687,857 | 688 | C34H49N5O8S |
| 138 | H | ~~(CH₂)₂-imidazole-N-propyl | 698,884 | 699 | C35H50N6O7S |

Example 3

Virological Properties of the Compounds of the Current Invention.

The compounds were tested in a cellular assay using the MT4-LTR-EGFP cells for anti-viral activity. The assay demonstrated that these compounds exhibit potent anti-HIV activity against a wild type laboratory HIV strain (WT IIIB-2-001). Because of the increasing emergence of drug resistant HIV strains, the present compounds were tested for their potency against clinically isolated HIV strains harboring several mutations. These mutations are associated with resistance to protease inhibitors and result in viruses that show various degrees of phenotypic cross-resistance to the currently commercially available drugs such as for instance saquinavir, ritonavir, nelfinavir, indinavir and amprenavir. The viral strains A, B, C and D contain mutations as indicated below in Table 2.

TABLE 2

| A | V003I, L010I, V032T, L033M, E035D, S037Y, M046I, R057R/K, Q058E, L063P, K070T, A071V, I072V, I084V, L089V |
|---|---|
| B | V003I, V032I, L035D, M036I, S037N, K043T, M046I, I047V, I050V, K055R, I057K, I062V, L063P, A071L, V082I, I085V, L090M, I093L |
| C | V003I L010I I013V G016A/G L019I L033F S037N M046I I050V F053L I054V K055R L063P A071V G073C V077I/V V082A L090M |
| D | V003I L010F I013V V032T S037N M046I I047V I050V L063P A071V I084V L089V T091A Q092R |

The cellular assay was performed according to the following procedure. HIV- or mock-infected MT4-LTR-EGFP cells were incubated for three days in the presence of various concentrations of the compounds according to the invention. Upon infection, the viral tat protein activates the GFP reporter. At the end of the incubation period, the GFP signal was measured. In the virus control samples (in the absence of any inhibitor) the maximal fluorescent signal was obtained. The inhibitory activity of the compound was monitored on the virus-infected cells and was expressed as $EC_{50}$. These values represent the amount of the compound required to protect 50% of the cells from virus infection. (Table 3).

TABLE 3

| Compound No. | WT IIIB-2-001 | A-2-001 | B-2-001 | D-2-001 | C-2-001 |
|---|---|---|---|---|---|
| 78 | 8.44 | 9.21 | 6.87 | 7.45 | 8 |
| 80 | 8.05 | 8.83 | 7.03 | 7.41 | 7.84 |
| 81 | 8.43 | 8.95 | 6.69 | 7.15 | 7.69 |
| 82 | 7.12 | 8.25 | 6.56 | 7.15 | 7.33 |
| 84 | 8.17 | 8.62 | 6.31 | 6.81 | 7.32 |
| 85 | 7.08 | 7.77 | 6.59 | 6.61 | 7.15 |
| 86 | 7.13 | 7.21 | 6.56 | 6.56 | |
| 87 | 7.71 | 7.62 | 6.63 | 6.55 | |
| 88 | 6 | 6.81 | 5.97 | 6.54 | 6.54 |
| 89 | 6.49 | 6.85 | 6.4 | 6.5 | 6.56 |
| 91 | 8.89 | 9.17 | 6.97 | 6.48 | 7.95 |
| 92 | 6.56 | 7.78 | 5.73 | 6.47 | 7.48 |
| 94 | 6.43 | 7.42 | 6.44 | 6.39 | 6.71 |
| 95 | 7.19 | 7.78 | 6.42 | 6.32 | 7.63 |
| 96 | 8.36 | 8.9 | 6.74 | 6.29 | |
| 97 | 6.56 | 7.14 | 6.41 | 6.21 | 6.95 |
| 98 | 8.34 | 9.31 | 5.96 | 6.18 | 7.01 |
| 100 | 8.78 | 9.14 | 7.05 | 6.17 | 7.33 |
| 101 | 9.1 | 7.92 | 6.58 | 6.16 | |
| 102 | 6.07 | 6.7 | 6.02 | 6.12 | 6.48 |
| 103 | 6.54 | 7.56 | 5.96 | 6.12 | |
| 105 | 7.22 | 7.76 | 6.27 | 6.09 | 6.77 |
| 106 | 6.57 | 7.14 | 6.03 | 6.08 | 6.68 |
| 107 | 7.84 | 8.28 | 6.59 | 6.05 | 7.47 |
| 109 | 7.64 | 8.43 | 6 | 6.01 | 6.57 |
| 113 | 7.16 | 7.53 | 6.03 | 5.85 | 6.24 |
| 114 | 8.42 | 8.52 | 6.37 | 5.71 | 7.48 |
| 115 | 7.09 | 7.53 | 5.67 | 5.71 | 6.38 |
| 118 | 7.18 | | 5.88 | 5.5 | 6.08 |
| 119 | 8.25 | 8.22 | 5.81 | 5.41 | 6.41 |
| 121 | 7.74 | 7.88 | 5.2 | 5.3 | 5.83 |
| 125 | 7.06 | 6.44 | 4.89 | 5.13 | 5.48 |
| 126 | 6.9 | 7.14 | 5.42 | 4.96 | 5.91 |
| 134 | 8.3 | 8.16 | 5.91 | | 6.27 |
| 135 | 8.26 | 8.71 | 6.73 | | |
| 137 | 6.87 | 8.62 | 6.54 | | 6.6 |
| 138 | 6.2 | 6.75 | 5.49 | | |

As reference compound has been used the compound called TMC 114 or darunavir with the following chemical structure, a new protease inhibitor under clinical investigation for the treatment of HIV-infections. Darunavir has the following chemical name: (3R,3aS,6aR)-hexahydrofuro[2,3-b]furan-3-yl N-[(1S,2R)-1-benzyl-2-hydroxy-3-(N1-isobutylsulfanilamido)propyl]carbamate

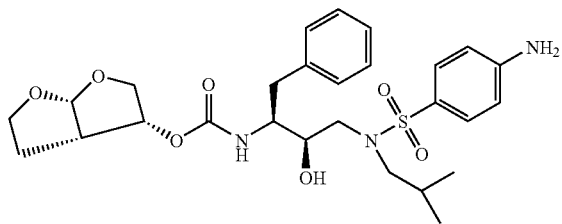

and the results obtained are as follows:

| pEC50_IIIB | pEC50-A | pEC50-B | pEC50-D | pEC50-C |
|---|---|---|---|---|
| 8, 17 | 8, 10 | 6, 07 | 5, 32 | 7, 05 |

Biovailability:
Caco-2 Permeability Assay for Intestinal Absorption

The permeability of different compounds is evaluated according to a Caco-2 test protocol as described by Augustijns et al. (Augustijns et al. (1998). *Int. J. of Pharm*, 166, 45-54) whereby, Caco-2 cells at cell passage number between 32 and 45 are grown in 24-well cell culture plates for 21 to 25 days. The integrity of the cell monolayer is checked by measuring the transepithelial electrical resistance (TEER). The test is performed at pH 7.4 and at 100 μM donor compound concentration.

Aqueous Solubility at Different pH Levels

The equilibrium solubility in simulated gastrointestinal solutions under thermodynamic conditions is a good measure for the solubility profile of the compound in the stomach and the different parts of the intestine. Simulated gastric fluid (SGF) (without pepsin) is set at pH of 1.5. Simulated intestinal fluids (SIF) (without bile salts) are set at pH 5, pH 6.5, pH 7 and pH 7.5. The experimental protocol uses 96-well flat-bottom microplates in which 1 mg of compound is added per well (stock solution in methanol) and evaporated to dryness. The compounds are resolubilized in SGF and SIF and incubated overnight on a horizontal shaking device at 37° C. After filtration, the compound concentrations are determined by UV-spectrophotometry.

Oral Availability in the Rat

The compounds are formulated as a 20 mg/ml solution or suspension in DMSO, PEG400 or cyclodextrine 40% in water. For most experiments in the rat (male and female rats), three dosing groups are formed: 1/single intraperitoneal (IP) dose at 20 mg/kg using DMSO formulation; 2/single oral dose at 20 mg/kg using PEG400 formulation and 3/single oral dose at 20 mg/kg using PEG400 formulation. Blood is sampled at regular time intervals after dosing and drug concentrations in the serum are determined using a LC-MS bioanalytical method. Serum concentrations are expressed in ng/mg. Serum concentration at 30 minutes (30') and at 3 hours (180') can be determined as these values reflect the extent of absorption (30') and the speed of elimination (180').

Boosting the Systemic Bioavailability

With the described type of compounds (protease-inhibitors), it is known that inhibition of the metabolic degradation processes can markedly increase the systemic availability by reducing the first-pass metabolism in the liver and the metabolic clearance from the plasma. This 'boosting' principle can be applied in a clinical setting to the pharmacological action of the drug. This principle can be also explored both in the rat or the dog by simultaneous administration of a compound that inhibits the Cyt-P450 metabolic enzymes. Known blockers are for example ritonavir and ketoconazole. Dosing a single oral dose of ritonvir at 5 mg/kg in the rat and the dog may result in an increase of the systemic availability.

Protein Binding Analyses:

Human serum proteins like albumin (HSA) or alpha-1 acid glycoprotein (AAG) are known to bind many drugs, resulting in a possible decrease in the effectiveness of those compounds. In order to determine whether the present compounds would be adversely affected by this binding, the anti-HIV activity of the compounds is measured in the presence of human serum, thus evaluating the effect of the binding of the protease inhibitors to those proteins.

Film-Coated Tablets
Preparation of Tablet Core

A mixture of 100 g of active ingredient, in casu a compound of formula (I or II), 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there is added 100 g microcrystalline cellulose and 15 g hydrogenated vegetable oil. The

The invention claimed is:

1. A compound having the formula

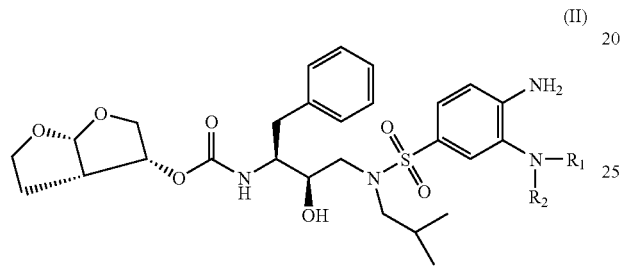

(II)

or N-oxide, salt, stereoisomeric form, racemic mixture, or ester thereof wherein $R_1$ and $R_2$ are, each independently, hydrogen, $C_{1-6}$-alkyl preferably $C_{1-4}$-alkyl optionally substituted by $C_{1-6}$alkyloxy, hydroxyl, $C_{3-7}$cycloalkyl, aryl, benzodioxolyl, $Het^1$, $Het^2$ or X wherein;

X is a carbon or nitrogen optionally substituted by —C(=O)—$NH_2$, $C_{1-6}$alkyloxy-C(=O)— or $C_{1-6}$alkyl-C(=O)—, Aryl as a group or part of a group is meant to include phenyl which may be optionally substituted with one or more substituents independently selected from $C_{1-6}$alkyl, $C_{1-6}$alkyloxy, amino$C_{1-6}$alkyl, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, $Het^1$, $Het^2$ optionally mono- or disubstituted aminocarbonyl, methylenedioxy, methylthio or methylsulfonyl, $Het^1$ as a group or part of a group is defined as a saturated or partially unsaturated monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl, $C_{1-6}$alkyloxy, amino$C_{1-6}$alkyl, halogen, hydroxy, acetyl, oxo, optionally mono- or disubstituted amino, optionally mono- or disubstituted aminoalkyl, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic cycle or heterocycle having 3 to 14 ring members; and wherein $Het^2$ as a group or part of a group is defined as an aromatic monocyclic, bicyclic or tricyclic heterocycle having preferably 3 to 14 ring members, more preferably 5 to 10 ring members and more preferably 5 to 6 ring members, which contains one or more heteroatom ring members selected from nitrogen, oxygen or sulphur and which is optionally substituted on one or more nitrogen and/or carbon atoms by $C_{1-6}$alkyl which may optionally substituted by $C_{3-7}$cycloalkyl, $C_{1-6}$alkyloxy, amino$C_{1-6}$alkyl, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl, $Het^1$ and an aromatic monocyclic, bicyclic or tricyclic cycle or heterocycle having 3 to 12 ring members.

2. A compound according claim 1 wherein
$R_1$ is hydrogen and
$R_2$ is $C_{1-6}$-alkyl preferably $C_{1-4}$-alkyl substituted by aryl which is substituted by halogen, or wherein said $C_{1-6}$-alkyl preferably $C_{1-4}$-alkyl is substituted by $Het^2$, or wherein said $C_{1-6}$-alkyl preferably $C_{1-4}$-alkyl is substituted by benzodioxolyl.

3. A compound according to claim 2 wherein
$R_1$ is hydrogen and
$R_2$ is $C_{1-4}$-alkyl substituted by aryl, which is di-substituted by fluoride, or wherein said $C_{1-4}$-alkyl is substituted by a saturated monocyclic heterocycle having 6 ring members containing nitrogen.

4. A compound according to claim 3 wherein the compound is (3-{[4-amino-3-(2,4-difluoro-benzylamino)-benzenesulfon-yl]-isobutyl-amino}-1-benzyl-2-hydroxy-propyl) carbamic acid hexahydro-furo[2,3-b]furan-3-yl ester or [3-({4-amino-3-[(pyridin-2-ylmethyl)-amino]-benzenesulfonyl}-isobu-tyl-amino)-1-benzyl-2-hydroxy-propyl]carbamic acid hexahydro-furo[2,3-b]furan-3-yl ester.

5. A pharmaceutical composition comprising an effective amount of at least one compound as claimed in claim 1 and a pharmaceutically tolerable excipient.

6. A method of inhibiting a protease of a multi-drug resistant retrovirus in a mammal infected with said retrovirus comprising administering a protease-inhibiting amount of a compound according to claim 1 to said mammal in need thereof.

7. A method of treating or combating infection or disease associated with multi-drug resistant retrovirus infection in a mammal comprising administering an effective amount of at least one compound according to claim 1 to said mammal.

8. A method of inhibiting multi-drug resistant retroviral replication comprising contacting a retrovirus with an effective amount of at least one compound according to claim 1.

9. A composition comprising at least (a) a compound of formula (I) or (II) as claimed in claim 1 and, (b) a second antiretroviral agent for the simultaneous, separate or sequential use.

* * * * *